United States Patent
Garretson et al.

(10) Patent No.: US 10,328,458 B2
(45) Date of Patent: Jun. 25, 2019

(54) COATING METHODS

(71) Applicant: MicroVention, Inc., Tustin, CA (US)

(72) Inventors: Joshua Garretson, San Diego, CA (US); John Belletto, Tustin, CA (US); Gregory M. Cruise, Rancho Santa Margarita, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

(21) Appl. No.: 13/781,385

(22) Filed: Feb. 28, 2013

(65) Prior Publication Data

US 2013/0243936 A1 Sep. 19, 2013

Related U.S. Application Data

(60) Provisional application No. 61/604,432, filed on Feb. 28, 2012.

(51) Int. Cl.

| | |
|---|---|
| *B05D 5/00* | (2006.01) |
| *C09D 171/08* | (2006.01) |
| *B05D 3/14* | (2006.01) |
| *C08G 18/48* | (2006.01) |
| *C08G 18/78* | (2006.01) |
| *C09D 175/08* | (2006.01) |
| *A61L 29/08* | (2006.01) |
| *A61L 31/10* | (2006.01) |

(52) U.S. Cl.
CPC .............. *B05D 5/00* (2013.01); *A61L 29/085* (2013.01); *A61L 31/10* (2013.01); *B05D 3/142* (2013.01); *C08G 18/4833* (2013.01); *C08G 18/7831* (2013.01); *C09D 171/08* (2013.01); *C09D 175/08* (2013.01); *A61L 2420/02* (2013.01); *B05D 2503/00* (2013.01)

(58) Field of Classification Search
CPC .. B32B 25/20; B32B 27/40; B32B 7/02; B32B 27/08; B32B 15/08; A61F 2/06; B02C 23/00; A61L 27/44
USPC .......... 156/60; 427/2.3, 2.28, 301, 318, 322, 427/534, 536, 393.5; 428/425.5, 334; 623/1; 241/16; 523/113
See application file for complete search history.

(56) References Cited

U.S. PATENT DOCUMENTS

| | | |
|---|---|---|
| 4,459,317 A | 7/1984 | Lambert |
| 4,487,808 A | 12/1984 | Lambert |
| 5,077,352 A | 12/1991 | Elton |

(Continued)

OTHER PUBLICATIONS

International Search Report and Written Opinion for International Application No. PCT/US2013/028380 filed on Feb. 28, 2013.

*Primary Examiner* — Andrew J Bowman
(74) *Attorney, Agent, or Firm* — K&L Gates LLP; Louis C. Cullman; Brian J. Novak

(57) ABSTRACT

Described herein are methods of coating both metallic and polymeric surfaces adding hydrophilicity comprising the steps mixing a coating composition comprising at least one polyol, at least one compound having at least two isocyanate groups, and an organic solvent; introducing nucleophilic functional groups on the surface thereby creating an active surface; subjecting the active surface to the coating composition thereby forming a coated surface; and curing the coated surface. Medical devices, for example, implantable medical devices can be coated by the methods described herein.

19 Claims, 1 Drawing Sheet

(56) References Cited

U.S. PATENT DOCUMENTS

| | | | |
|---|---|---|---|
| 5,225,267 A * | 7/1993 | Ochi | B32B 15/08 |
| | | | 428/214 |
| 5,281,468 A | 1/1994 | Klier et al. | |
| 5,545,208 A * | 8/1996 | Wolff et al. | 623/1.22 |
| 5,662,960 A * | 9/1997 | Hostettler et al. | 427/2.3 |
| 5,776,661 A | 7/1998 | Casaletto | |
| 5,804,299 A * | 9/1998 | Nakata | C08J 7/047 |
| | | | 200/333 |
| 5,888,656 A * | 3/1999 | Suzuki et al. | 428/425.5 |
| 6,030,656 A | 2/2000 | Hostettler et al. | |
| 6,083,257 A * | 7/2000 | Taylor | A61F 2/90 |
| | | | 623/1.46 |
| 6,099,562 A | 8/2000 | Ding | |
| 6,673,453 B2 | 1/2004 | Beavers | |
| 6,803,069 B2 | 10/2004 | Patnaik et al. | |
| 7,008,979 B2 | 3/2006 | Schottman | |
| 7,264,859 B2 | 9/2007 | Rouns | |
| 7,494,687 B2 | 2/2009 | Cox | |
| 7,544,381 B2 | 6/2009 | Kangas | |
| 7,544,673 B2 | 6/2009 | DeWitt | |
| 7,553,546 B1 | 6/2009 | Tan | |
| 7,770,828 B2 * | 8/2010 | Matsumoto et al. | 241/16 |
| 2002/0082679 A1 * | 6/2002 | Sirhan | A61F 2/91 |
| | | | 623/1.15 |
| 2003/0069647 A1 * | 4/2003 | Desmond, III | A61F 2/94 |
| | | | 623/23.7 |
| 2010/0105799 A1 * | 4/2010 | Rudd | A61L 27/446 |
| | | | 523/113 |
| 2010/0236684 A1 * | 9/2010 | Garlough | 156/60 |
| 2011/0117282 A1 | 5/2011 | Bernard | |

* cited by examiner

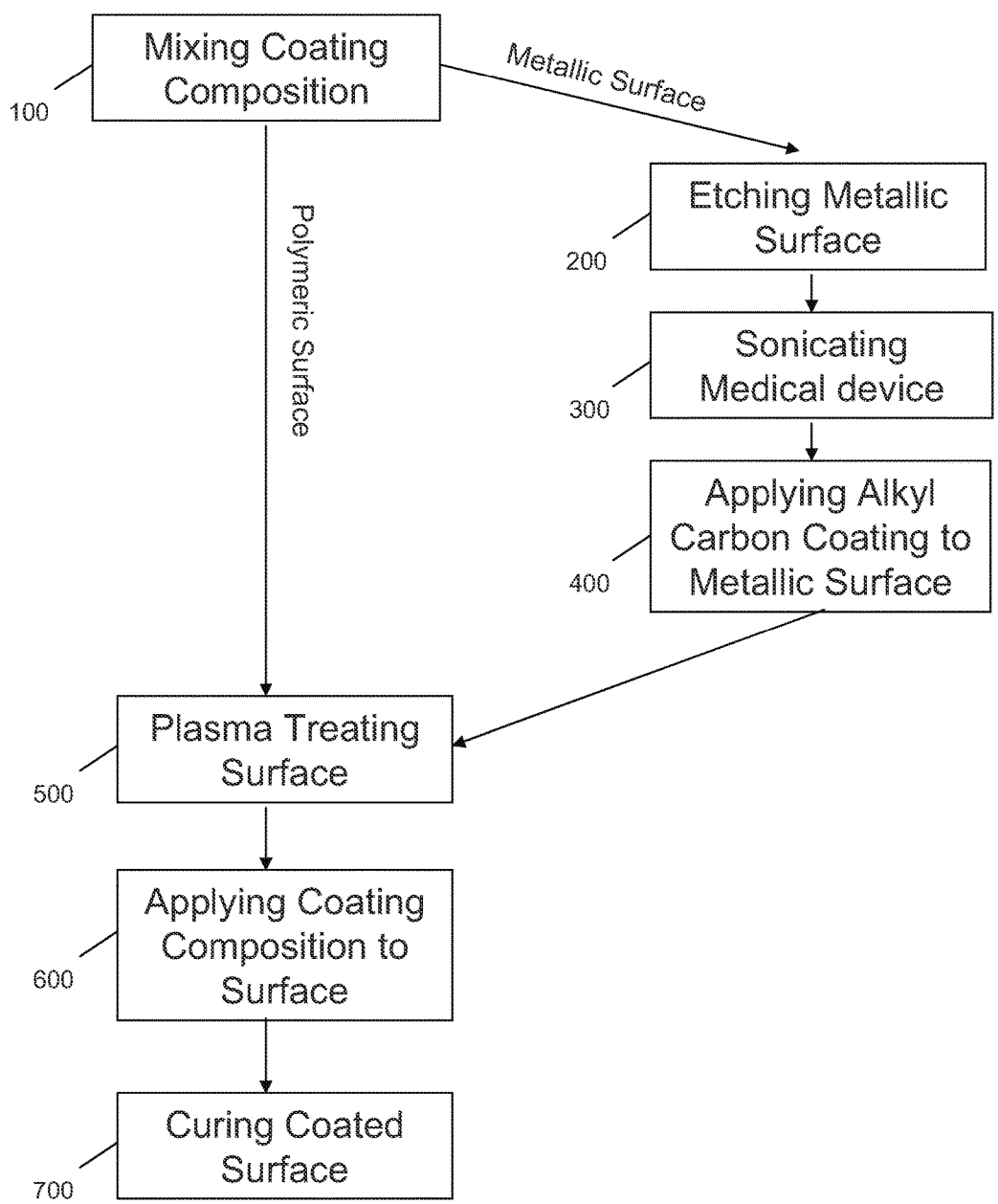

COATING METHODS

CROSS REFERENCE TO RELATED APPLICATIONS

This application claims the benefit of U.S. provisional patent application No. 61/604,432, filed Feb. 28, 2012, the entire disclosure of which is incorporated herein by reference.

FIELD

The present invention relates generally to the preparation and application of lubricious hydrophilic coatings to medical devices exposed to aqueous environments.

BACKGROUND

Many currently marketed biomedical devices are manufactured using various hydrophobic polymers and/or metallic blends to achieve desired physical properties and optimize performance. The coatings described herein demonstrate that frictional resistance and durability can be effectively achieved with a single coating application including a polyol and an aliphatic multi-isocyanate that is introduced to a prepared substrate surface.

SUMMARY

Generally described herein are methods of coating surfaces thereby adding hydrophilicity comprising the steps a) mixing a coating composition comprising at least one polyol, at least one compound having at least two isocyanate groups and an organic solvent; b) introducing nucleophilic functional groups on the surface thereby creating an active surface; c) subjecting the active surface to the coating composition thereby forming a coated surface; and d) curing the coated surface.

Methods are also described of coating a surface comprising contacting a coating composition with a surface, wherein the coating composition comprises at least one polyol, at least one compound having at least two isocyanate groups and an organic solvent with a surface, and wherein the surface has been treated with a plasma.

In another embodiment, the methods can include coating of implantable medical device surfaces thereby adding hydrophilicity comprising the steps a) providing an implantable medical device; b) mixing a coating composition comprising at least one polyol, at least one compound having at least two isocyanate groups and an organic solvent; c) plasma treating a surface of the implantable medical device thereby creating an active surface; d) subjecting the active surface to the coating composition thereby forming a coated surface; e) curing the coated surface; and f) forming a coated implantable medical device that is lubricious when contacted with an aqueous environment.

In some embodiments, the surface is polymeric. In others, the surface can be glass or metallic. If metallic, the methods can further include a step comprising applying at least one alkyl carbon containing coating such as an alkyl silane coating toa the metallic surface.

In some embodiments, the at least one polyol is selected from poly(ethylene glycol), poly(tetramethylene oxide), ethoxylated trimethylol propane, glycerin, poly(hydroxyethyl methacrylate), poly(vinyl alcohol) and combinations thereof. In others, the compound having at least two isocyanate groups is selected from 1,4-tetramethylene di-isocyanate, 1,6-hexamethylene di-isocyanate (HDI), trifunctional biuret, isocyanurate derivatives of HDI, p-tetramethylxylene di-isocyanate, trans 1,4-cyclohexylene di-isocyanate, m-xylene di-isocyanate, DESMODUR.RTM. N-75 BA/X and combinations thereof.

In another embodiment, the implantable medical device is selected from catheters, introducer sheaths, stents, embolic pushers, guide wires, overcoils and combinations thereof.

BRIEF DESCRIPTION OF THE DRAWINGS

FIG. 1 illustrates a flow chart of exemplary coating methods according to the present description.

DETAILED DESCRIPTION

Described herein are methods for forming durable lubricious hydrophilic coatings on substrate surfaces intended for exposure to aqueous environments. The hydrophilic coatings can be prepared in fewer steps than methods used in the art. Fewer production steps may save both time and/or money in an industrial setting and can create a unique coating material formation. A coating solution can be created in an organic solvent prior to a coating step by combining at least one polyol and at least one compound containing at least two isocyanate groups. This is different than other coating methods requiring long grafting steps where an isocyanate is bonded to a surface and then a polymer is grafted onto the bound isocyanate.

Some current coating methods take a day or more to grow a hydrophilic polymer onto a surface. In contrast, the present description may provide a two step method of fuctionalizing the surface to be coated and dipping that functionalized surface into a coating composition that has already been polymerized. This can speed up the coating process. The present methods can also be advantageous because a primer base coat may not be needed. Commonly, base coats such as parylene are used to prepare a surface for coating. However, in some embodiments, no such coating is needed; this can save both time and money in manufacturing. Also, the coatings described herein may not require a top coat.

The hydrophilic coatings described herein can also be rendered lubricious when placed in contact with an aqueous environment. This lubricity allows implantable medical devices to be easily guided through bodily tissues or against, inside or next to another medical device.

Further, the coatings described herein do not delaminate, flake or degrade during normal use. Normal use can include preparation and implantation. Some coatings described herein can be non-resorbable. As used herein, the term "non-resorbable" includes a coating material that cannot be readily degraded, cannot be substantially degraded or cannot be absorbed by bodily tissues. Such non-resorbable coatings can be implanted and remain intact while tissues grow around and even over the coatings. In other embodiments, the coatings can be biodegradable and degrade over a period of time. For example, the coatings can degrade over about 30 days, about 60 days, about 90 days about 120 days, about 1 year, about 5 years or any number of years in a range defined by, or between, any of these values.

Also, the coatings can be biocompatible. As used herein "biocompatible" shall mean any material that is adequate for use in intimate contact with tissues. For example, a biocompatible coating may avoid some inflammation, infection, fibrotic tissue formation or cell death.

Substrate surfaces can generally include surfaces of medical devices. Even more specifically, surfaces can include surfaces of implantable medical devices which can come into contact with aqueous environments are likely to need the presently described coatings. Exemplary devices include, but are not limited to, catheters, introducer sheaths, stents, embolic pushers, guide wires, overcoils and the like. Additionally, systems including multiple implantable medical devices can be coated together.

These substrate surfaces can be metal, glass, polymeric (e.g. plastic) or both. Metals can include bare metals and metal alloys such as, but not limited to, steel, stainless steel, iron, nitinol, aluminum, brass, copper, titanium, and barium. Polymers can include, but are not limited to, thermosets, injection molded polymer and the like. Examples of polymers can include grilamide, polyether ether ketone, Teflon, polyethelene, polyester, polycarbonate, nylon, and rubber. Examples of glass material can include quartz, borosilicate glass, crystal, diamond, cubic zirconium, and the like. Depending on the composition of the surface, different variations of the herein described coating methods can be used. For example, a polymeric medical device surface may not need to be chemically etched. In fact, such etching may be harmful to the medical device. As such, chemical etching may be avoided on particular device surfaces.

FIG. 1 illustrates one embodiment of a process used to coat substrate surfaces. This process is not limiting and may be rearranged or additional or optional steps may be added. In some embodiments, steps can be rearranged based on the skill and knowledge of an artisan. Generally, as a first step 100 a coating composition is prepared including at least one polyalcohol or polyol and at least one compound containing at least two isocyanate groups. Preparing the coating composition before further processing can allow time for the composition to fully form prior to actual coating. In other words, the coating composition can form while the surface is prepared as described below. However, the coating composition formation step can also be performed just prior to surface coating.

The coating composition can be suspended or dissolved in an organic solvent. The function of organic solvent in the coating composition can be to dissolve or disperse any of the polyalcohol(s) (polyols), multi-isocyanate compound(s) and catalyst(s). The solvent can serve as a carrier agent for the cross-linked polyols. Solvent selection can be determined by the solubility of the coating composition's components as well as solvent volatility. A preferred solvent can be dichloromethane. Other possible solvents include but are not limited to tetrahydrofuran, acetonitrile, chloroform, dioxane, benzene, toluene, dimethyl formamide and dimethylsulfoxide.

A function of the polyol can be to impart desired physical properties and provide the coating's structural framework. The polyol used in the coating composition can be any molecule with at least two hydroxyl groups envisioned by one skilled in the art. Exemplary polyols include linear diol polymers and branched polyols. The polyols described herein can have a hydroxyl number between about 10 mg KOH/g and about 1,000 mg KOH/g, about 20 mg KOH/g and about 500 mg KOH/g, about 50 mg KOH/g and about 100 mg KOH/g or any hydroxyl number in a range defined by, or between, any of these values.

In general, polyols can include any multi-hydroxyl containing compound. Example polyols can include those having a structure

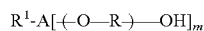

wherein R and $R^1$ are each independently a $C_{1-10}$ optionally substituted alkyl group;

m is 2, 3, 4, 5, 6 or more;
A is

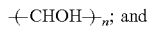

n is 2, 3, 4, 5, 6 or more.

The term "optionally substituted" can include a feature that may have no substituents (i.e. be unsubstituted) or may have one or more substituents. A feature that is "substituted" has one or more substituents. The term "substituent" has the ordinary meaning known to one of ordinary skill in the art. A substituent generally includes at least 1, or 1-5, 1-10, 1-20, or 1-30, atoms independently selected from: C, N, O, S, P, Si, F, Cl, Br, I, or a combination thereof, and may include hydrogen atoms. In some embodiments a substituent may comprise at least one of: C, N, O, S, P, Si, F, Cl, Br, and I, and/or may have a molecular weight of: at least about 15; and/or less than about 500, about 300, about 200, about 150, about 100, about 75, or about 50. In some embodiments, the substituent has at least 1 carbon atom or at least 1 heteroatom, and has about 0-10 carbon atoms and about 0-5 heteroatoms independently selected from: N, O, S, F, Cl, Br, I, and combinations thereof. In some embodiments, each substituent consists of: about 0-20 carbon atoms; about 0-47 hydrogen atoms; 0, 1, 2, 3, 4, or 5 oxygen atoms; 0, 1, or 2 sulfur atoms; 0, 1, 2, or 3 nitrogen atoms; 0 or 1 silicon atoms; 0, 1, 2, 3, 4, 5, 6, or 7 fluorine atoms; 0, 1, 2, or 3 chlorine atoms; 0, 1, 2, or 3 bromine atoms; and 0, 1, 2, or 3 iodine atoms. Examples include, but are not limited to, alkyl, alkenyl, alkynyl, carbazolyl, cycloalkyl, cycloalkenyl, cycloalkynyl, aryl, diarylamino, heteroaryl, heteroalicyclyl, aralkyl, heteroaralkyl, (heteroalicyclyl)alkyl, hydroxy, protected hydroxy, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, and amino, including mono- and di-substituted amino groups, and the protected derivatives thereof.

In some embodiments, substituents may include, but are not limited to, $C_{1-10}$ alkyl such as methyl, ethyl, propyl isomers (e.g. n-propyl and isopropyl), cyclopropyl, butyl isomers, cyclobutyl isomers (e.g. cyclobutyl, methylcyclopropyl, etc.), pentyl isomers, cyclopentyl isomers, hexyl isomers, cyclohexyl isomers, heptyl isomer, cycloheptyl isomers, etc; alkoxy such as —$OCH_3$, —$OC_2H_5$, —$OC_3H_7$, —$OC_4H_9$, —$OC_5H_{11}$, —$OC_6H_{13}$, —$OC_7H_{15}$, etc.; halo, such as F, Cl, Br, I, etc.; $C_{1-10}$ haloalkyl, including perfluoroalkyl such as —$CF_3$, —$C_2F_5$, —$C_3F_7$, —$C_4F_9$, etc.; $C_{1-10}$ acyl such as formyl, acetyl, benzoyl, etc.; $C_{1-10}$ amides attaching at the carbonyl or nitrogen atom such as —$NCOCH_3$, —$CONHCH_2$, etc.; $C_{1-10}$ esters attaching at the carbonyl or oxygen atom such as —$OCOCH_3$, —$CO_2CH_2$, etc.; $C_{1-10}$ carbamates attaching at the nitrogen atom or oxygen atom; cyano; cyanate; isocyanate; nitro; etc.

In some embodiments, the substituents may be selected from: F, Cl, $C_{1-6}$ alkyl, —O—$C_{1-6}$ alkyl, ON, $NO_2$, and $CF_3$.

In other embodiments, the polyol can have a structure

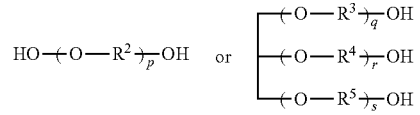

wherein $R^2$, $R^3$, $R^4$ and $R^5$ are each independently $C_tH_u$ wherein t and u are each independently 2, 3, 4, 5, 6, 7 or 8; and p, q, r and s are each independently 2, 3, 4, 5, 6, 7, 8 or more.

In some embodiments, $R^2$, $R^3$, $R^4$ and $R^5$ can each independently be $C_2H_4$, $C_3H_6$, $C_5H_{10}$ or $C_6H_{12}$.

Further, polyols can include, but are not limited to, polyethers such as polyethyleneoxide, poly(ethylene glycol) (PEG), poly(tetramethylene oxide), ethoxylated trimethylol propane, glycerin, poly(hydroxyethyl methacrylate) and poly(vinyl alcohol). Poly(ethylene glycol) can be utilized in a linear diol form as well as a branched polyol. Effective molecular weights of polyols can be about 5,000 g/mol, about 10,000 g/mol, about 15,000 g/mol, about 20,000 g/mol, about 25,000 g/mol, or can range from about 3,500 g/mol to about 20,000 g/mol, about 5,000 g/mol to about 15,000 g/mol, about 8,000 g/mol to about 12,000 g/mol, or any molecular weight in a range defined by, or between, any of these values.

In one embodiment, the polyol is PEG. A preferred embodiment can be a linear poly(ethylene glycol) with a molecular weight of about 10,000 g/mol.

In other embodiments, the polyol can be a plant derived or organic polyol such as a natural oil polyol derived from vegetable oils. Caster oil (ricinoleic acid) is an example of a vegetable oil that can produce a polyol. Other vegetable oils can include soy bean oil, corn oil, cotton seed oil, sunflower oil, castor oil, palm tree oil, peanut oil, palm oil and others while the animal oils are beef oil, pork oil, fish oil, hardened oil and combinations thereof.

A function of the multi-isocyanate containing compounds can be to provide chemically reactive cross-linking groups capable of bonding the polyols to each other and the substrate surface. Chemical reaction of the species can create a polyurethane network of polymers that once hydrated disperses frictional energy as molecular movement of the polymer chains and associated hydration molecules. Aliphatic tri-isocyanate, aliphatic di-isocyanate, aromatic di-isocyanate aromatic poly-isocyanate or a combination thereof can be used as cross-linking agents.

In one embodiment, the at least one isocyanate can be but is not limited to 1,4-tetramethylene di-isocyanate, methylene diphenyl diisocyanate, toluene diisocyanate, isophorone diisocyanate, DESMODUR.RTM. N-75 BA/X (Bayer, Germany), 1,6-hexamethylene di-isocyanate(HDI), hexamethylene diisocyanate, 1,2-ethanediisocyanate, 1,3-propanediisocyanate, 1,4-butanediisocyanate, 1,5-pentanediisocyanate, lysine diisocyanate and 1,4-cyclohexanediisocyanate, 2,4- and 2,6-tolylene diisocyanate and isomer mixtures thereof, o-and m-xylylene diisocyanate, 1,5-naphthylene diisocyanate, 1,4-cyclohexylene diisocyanate, dicyclohexylmethane diisocyanate and mixtures thereof, dicyclohexylmethane diisocyanate, trifunctional biuret and isocyanurate derivatives of HDI, p-tetramethylxylene di-isocyanate, m-xylene di-isocyanate or combinations thereof. In a preferred embodiment, an exemplary multi-isocyanate can be DESMODUR.RTM. N-75 BA/X. DESMODUR.RTM. N 75 BA/X is an aliphatic polyisocyanate resin based on hexamethylene diisocyanate (HDI) and dissolved in n-butyl acetate and xylene (1:1).

Ratios of polyol to isocyanate can exist that provide a durable coating material. Ratios can be about 1,000:1, about 500:1, about 250:1, about 100:1, about 50:1, about 25:1, about 10:1, about 5:1, about 2:1, about 1:1, about 1:2, about 1:5, about 1:10, about 1:25, about 1:50, about 1:100, about 1:250, about 1:500, about 1:1,000 or any ratio in a range defined by, or between, any of these values.

Although optional, one or more catalyst can also be included. One function of a catalyst can be to lower the activation energy of the reaction facilitating rapid cross-linking polyol to multi-isocyanate as well as speed up the reaction time of coating-to-surface bonding. In one embodiment, concerted metallic catalysis can be used to lower activation energy and speed up the reaction time. In other embodiments, a stepwise base catalysis can be used to catalyze the reaction. However, despite the advantages of using a catalyst to speed up the reaction, in some embodiments, a catalyst is not used.

Possible catalysts can include dialkyltin diacylates, dialkyl tin oxides, stannous acylates, amine based catalysts like 1,4-diazabicyclo[2.2.2]octane (DABCO) and combinations thereof. Metal catalysis is thought to work through a concerted joining of the reactive species while amine based catalysis is thought to work through step wise acid-base catalytic transfer of hydrogen ions. In one embodiment, a preferred catalyst can be dibutyltin dilaurate.

Substrate surfaces that are to be coated can be treated (pre-treated) by application of one or more surface treatments. In one embodiment, lubricious hydrophilic coatings can be applied directly to functionally prepared plastic surfaces.

As an optional second step 200, a metallic substrate can be cleaned in an etching solution. The etching solution can contain an acid appropriate to etch the surface of the substrate and can further include an oxidizing agent such as hydrogen peroxide. The etching solution can include a strong acid, such as sulfuric acid, chromosulfuric acid, nitric acid, hydrochloric acid or combinations thereof. The etching can be performed at room temperature or at an elevated temperature above room temperature such as at about 25° C., about 30° C., about 35° C., about 40° C., about 45° C., about 50° C., about 60° C., about 70° C., about 80° C., about 90° C., about 100° C., about 110° C., about 120° C. or any temperature in a range defined by, or between, any of these values. For example, a metallic substrate can be cleaned at 25° C. using a 3 parts $H_2SO_4$/1 part $H_2O_2$ etching solution. In another embodiment, etching can be achieved using an etching solution at 80° C. In another embodiment the metallic substrate can be cleaned with either chromosulfuric acid or nitric acid.

Etching metallic substrates in some instances can remove debris from the surface while creating a uniform oxidation state prior to silanization. Etching conditions can be determined by the substrate's metallic composition. For hard metals such as stainless steel, the substrate can be emerged in an etching solution of $H_2SO_4/H_2O_2$ and held at 80° C. for one hour. In one embodiment, a preferred ratio of sulfuric acid to hydrogen peroxide is 3:1. Softer metallic blends, such as nitinol, are not as resilient to oxidative chemical stress and/or experience leeching at higher temperatures, and incubation is preformed at 25° C.

The substrate, be it plastic, glass or metal, can also be sonicated 300 to clean the substrate surface of foreign debris and remove any residual etching solution if used. Sonication of plastic is optional and in one embodiment plastic is not sonicated. In another embodiment, the metal is sonicated. A preferred method can be to sonicate the substrate in organic solvent(s) for a total of about one hour. A preferred solvent sequence can be 200 proof ethanol, acetone and then dichloromethane. In one embodiment, the substrates are sonicated in water.

After a metallic substrate surface has been cleaned thoroughly, the surface can then be subjected to silanization 400. This silanization can form a surface containing alkyl carbons, rendering it reactive to plasma gas treatment. The compositions can contain silanes in alcohol with or without water to facilitate reaction of the silanes both with each other and the surface of the substrate. The silane solution can, in some embodiments, be anhydrous to preserve the pendant functionality(ies) of the particular silane chosen. The coating composition can also include compounds that can install alkyl carbons, nucleophiles, electrophiles, or a combination thereof.

Silanes can include trialkoxyalkyl silanes such as, but not limited to, trimethoxy(octadecyl) silane, triethoxy(octyl) silane, trichloro(octadecyl) silane or similar silane with a pendant alkyl group(s) in a 3-5% concentration.

Substrates can be incubated in a 1-10% silane, 1% acetic acid in ethanol that may or may not contain 2% water for about 18 hours. Heat curing may be required and can be achieved by dry baking the substrate at about 135° C. for an hour.

Alternatively, the substrate surface can be rendered directly functional to bonding with the hydrophilic coating by choice of an appropriate functional group pendant to the silane or other metal reactive coating agent. Compounds such as (trialkoxysilyl)alkyl isocyanates, (trialkoxysilyl)alkyl alcohols, or (trialkoxysilyl)alkyl amines can install isocyanates to the metal surface which can directly bond to coating composition polymers with pendant alcohols. In one embodiment, the compound can be 3-(triethoxysilyl)propyl isocyanate.

Next, the substrate surfaces can be subjected to functional preparation by plasma treatment 500. The plasma can be argon, oxygen, allylamine or allylalcohol gas. In some embodiments, the substrates do not need plasma treatment before application of a lubricious hydrophilic coating.

The plasma treatment can be a conventional corona treatment wherein a surface can be modified using a low temperature corona discharge plasma to impart changes in the properties of a surface. The corona plasma can be generated by the application of high voltage to sharp electrode tips which forms plasma at the ends of the sharp tips. A linear array of electrodes can often be used to create a curtain of corona plasma.

Another form of plasma treatment that can be performed is atmospheric plasma treatment. Like corona treatment, this treatment may use one or more high voltage electrodes which charge the surrounding blown gas molecules and ionizes them. However in atmospheric plasma systems, the overall plasma density can be much greater which can enhance the rate and degree that the ionized molecules are incorporated onto a materials' surface.

Flame plasma can also be used as a plasma treatment. Flame plasma can generate more heat than other treating processes, but materials treated through this method can have a longer shelf-life. When flame plasma is used, the temperature can be held sufficiently low to prevent damage from the surfaces to be coated. These plasma systems are different from air plasma systems because flame plasma occurs when flammable gas and surrounding air are combusted into an intense blue flame. Objects' surfaces are polarized from the flame plasma affecting the distribution of the surface's electrons in an oxidation form.

Chemical plasma can also be used to plasma treat the surfaces. Chemical plasma is based on the combination of air plasma and flame plasma. Chemical plasma fields are generated from electrically charged air.

Plasma treatment can create electrophilic species on the surface like aldehydes, esters and carboxylic acids which, like isocyanates, are reactive towards nucleophilic attack thus facilitating bonding of the hydrophilic coating.

In one embodiment, plasma treatment can increase reactivity of the surface to the coating composition by installing nucleophiles. Nucleophilic groups to be added to a substrates surface are oxygen species such as alcohols or nitrogen species such as amines. The plasma treatment processing parameters can be fine tuned by a skilled practitioner for a particular coating application.

For example, gas flow rates can range from about 100 sccm to about 300 sccm, about 150 sccm to about 250 sccm, about 175 sccm to about 225 sccm or any flow rate in a range defined by, or between, any of these values. In one example embodiment, the gas flow is about 195 sccm. Power outputs can range from about 25 watts to about 250 watts, about 75 watts to about 200 watts, about 100 watts to about 150 watts or any power output in a range defined by, or between, any of these values. In one example embodiment, the power output is about 126 watts. Plasma field exposure time can range from about 60 seconds to about 1,000 seconds, about 120 seconds to about 500 seconds, about 250 seconds to about 400 seconds or any exposure time in a range defined by, or between, any of these values. In one example embodiment, the exposure time is about 300 seconds.

In one example embodiment, the parameters can be a gas flow rate of 195±10 sccm, a power of 126±5 watts to create the plasma field, and a 5 minutes±30 second plasma field exposure time degassed by a 500±200 mtorr vacuum. Suitable gases can include but are not limited to allylamine, allylalcohol, oxygen and argon.

After plasma treatment or another surface functionalization method, the surface can be subjected 600 to the coating composition. Methods for subjecting the surface to the coating composition can include dipping, brushing, spray coating, sputtering, running under a stream of coating composition, chemical vapor deposition and the like. In one example embodiment, the substrate is dipped into a coating composition and dwelled for about 10 seconds, about 20 seconds, about 30 seconds, about 45 seconds, about 1 min, about 2 minutes, about 3 minutes, about 4 minutes, about 5 minutes, about 10 minutes, about 20 minutes, about 30 minutes, about 60 minutes, about 120 minutes, about 240 minutes or any time in a range defined by, or between, any of these values.

After the substrate has been subjected to the coating composition and time has elapsed for the coating to associate with the activated surface of the substrate, the coating can be allowed to cure. Curing 700 can occur at room temperature or at an elevated temperature. Curing times can range from about 1 minute to about 1 day, from about 5 minutes to about 6 hours, from about 20 minutes to about 2 hours, from about 60 minutes to about 90 minutes or any curing time in a range defined by, or between, any of these values.

Thermal curing can then be used to drive reaction of the coating polymers with the surface reactive groups and to remove solvent after the coating has been bound to the substrate surface facilitating storage for later use. Curing temperature and duration can be variable based on the solvent requirements as well as substrate stability. The bake curing times can range from about 30 minutes to about 2.5 hours. Curing temperatures can range from about 25° C. to about 200° C. A preferred embodiment can be a 45 minute cure at 60° C.

After the coatings have been cured, the coated medical devices can be packaged and sterilized as per industry standards with little to no degradation of the lubricious coatings. Even after about 1 year, about 2 years about 5 years or longer, the coatings can still become lubricious when subjected to an aqueous environment.

The coatings described can reduce or substantially reduce a surface's lubricity. Lubricity can be reduced about 50%, about 60%, about 70%, about 75%, about 80%, about 85%, about 86%, about 87%, about 88%, about 89%, about 90%, about 91%, about 92%, about 93% about 94%, about 95%, about 96%, about 97%, about 98%, about 99%, between about 50% and about 95%, between about 80% and about 97%, between about 90% and about 97%, between about 85% and about 97%, at least about 80%, at least about 90%, or any range bound by or including any of the listed values.

Lubricity can be measured by placing a coated sample in a water bath and pulling it through a 60D silicone pad for 100 mm at a speed of about 25 mm/s. The average force required to pull a coated sample can be between about 10 g, about 12 g, about 14 g, about 16 g, about 18 g, about 20 g, about 22 g, about 24 g, about 26 g, about 28 g, about 30 g, about 32 g, about 34 g, about 36 g, about 38 g, about 40 g, about 42 g, about 44 g, between about 10 g and about 44 g, between about 12 g and about 40 g, between about 20 g and about 30 g, between about 30 g and about 4 g, between about 26 g and about 36 g, or any range bound by or including any of the listed values. In some embodiments, different coated materials can exhibit different lubricity. For example, coated polymeric tubing can have an average force of between about 12.6 g and about 19.1 g. More specifically, coated grilamide can have an average force of between about 17.5 g and about 19.1 g, and coated teflon/polyethylene can have an average force between about 12.6 g and about 14 g. In another embodiment, coated metal or metal alloy tubing can have an average force of between about 23.4 g and about 39.8 g. More specifically, coated stainless steel can have an average force of between about 23.4 g and about 25.5 g, and coated nitinol can have an average force between about 32.4 g and about 39.8 g.

EXAMPLE 1

Argon Plasma Treated Grilamid

A 12" length of grilamid tubing (0.025" ID) underwent argon gas plasma treatment to increase nucleophilic functionality. The argon gas plasma treatment was performed with a gas flow rate of 195 sccm at 126 watts under 500 mtorr of pressure for 5 minutes.

After treatment, the tubing was mechanically dipped into a cross-linked polyol coating formulation prepared by combining 10 g poly(ethylene glycol), mean molecular weight 10,000 (Polysciences, Inc.), 0.641 g DESMODUR® N-75 BA/X (Bayer Corp.), 148 µL dibutyltin dilaurate, 95% (Sigma-Aldrich Co.), 100 mL dichloromethane (Sigma-Aldrich Co.) into a 250 mL Erlenmeyer flask. The tubing dwelled in the coating formulation for two minutes before being extracted.

After extraction, the coated grilamid section was cured at 60° C. for 45 minutes. The resulting product was an alkyl carbon containing surface that was rendered to be lubricious when exposed to an aqueous solution.

EXAMPLE 2

Argon Plasma Treated Polyether Ether Ketone

A 12" length of polyether ether ketone (PEEK) mandrel (0.014" ID) underwent argon gas plasma treatment to increase nucleophilic functionality. The argon gas plasma treatment was performed with a gas flow rate of 195 sccm at 126 watts under 500 mtorr of pressure for 5 minutes.

The mandrel was mechanically dipped into a cross-linked polyol coating formulation prepared by weighing 10 g poly(ethylene glycol), mean molecular weight 10,000 (Polysciences, Inc.), 0.641 g DESMODUR® N-75 BA/X (Bayer Corp.), 148 µL dibutyltin dilaurate, 95% (Sigma-Aldrich Co.), and 100 mL dichloromethane (Sigma-Aldrich Co.) into a 250 mL Erlenmeyer flask. The tubing dwelled in the coating formulation for two minutes before being extracted.

After extraction, the coated mandrel section was cured at 60° C. for 45 minutes. The resulting product was an alkyl carbon containing surface that was rendered to be lubricious when exposed to an aqueous solution.

EXAMPLE 3

Oxygen Plasma Treated Teflon/Polyethylene Coextrusion

A 6" length of Teflon-Polyethylene coextrusion underwent oxygen gas plasma treatment to increase nucleophilic functionality.

The coextrusion was mechanically dipped into a cross-linked polyol coating formulation prepared by weighing 10 g poly(ethylene glycol), mean molecular weight 10,000 (Polysciences, Inc.), 0.321 g DESMODUR® N-75 BA/X (Bayer Corp.), 74 µL dibutyltin dilaurate, 95% (Sigma-Aldrich Co.), and 100 mL dichloromethane (Sigma-Aldrich Co.) into a 250 mL Erlenmeyer flask. The tubing dwelled in the coating formulation for two minutes before being extracted.

After extraction, the coated coextrusion section was cured at 60° C. for 45 minutes. The resulting product was an alkyl carbon containing surface that was rendered to be lubricious when exposed to an aqueous solution.

EXAMPLE 4

Allylamine Plasma Treated Grilamid

A 12" length of grilamid tubing (0.025" ID) underwent allylamine plasma treatment to increase nucleophilic functionality.

The grilamid was mechanically dipped into a cross-linked polyol coating formulation prepared by weighing 10 g poly(ethylene glycol), mean molecular weight 10,000 (Polysciences, Inc.), 0.641 g DESMODUR® N-75 BA/X (Bayer), 148 µL dibutyltin dilaurate, 95% (Sigma-Aldrich Co.), and 100 mL dichloromethane (Sigma-Aldrich Co.) into a 250 mL Erlenmeyer flask. The tubing dwelled in the coating formulation for two minutes before being extracted.

After extraction, the coated grilamid section was cured at 60° C. for 45 minutes. The resulting product was an alkyl carbon containing surface that was rendered to be lubricious when exposed to an aqueous solution.

EXAMPLE 5

Allylalcohol Plasma Treated Grilamid

A 12" length of grilamid tubing (0.025" ID) underwent allylalcohol plasma treatment to increase nucleophilic functionality.

The grilamid was mechanically dipped into a cross-linked polyol coating formulation prepared by weighing 10 g poly(ethylene glycol), mean molecular weight 10,000 (Polysciences, Inc.), 0.641 g DESMODUR® N-75 BA/X (Bayer), 148 µL dibutyltin dilaurate, 95% (Sigma-Aldrich Co.), and 100 mL dichloromethane (Sigma-Aldrich Co.) into a 250 mL Erlenmeyer flask. The tubing dwelled in the coating formulation for two minutes before being extracted.

After extraction, the coated grilamid section was bake cured at 60° C. for 45 minutes. The resulting product was an alkyl carbon containing surface that was rendered to be lubricious when exposed to an aqueous solution.

EXAMPLE 6

Argon Plasma Treated Stainless Steel Silanized with Trimethoxy(Octadecyl) Silane A 7" length of 304 stainless steel mandrel (0.018" ID) was dip coated in a 3% trimethoxy(octadecyl) silane solution to apply an alkyl surface. Then, the mandrel underwent argon gas plasma treatment to increase nucleophilic functionality. The argon gas plasma treatment was performed with a gas flow rate of 195 sccm at 126 watts under 500 mtorr of pressure for 5 minutes.

The sample was mechanically dipped into a cross-linked polyol coating formulation prepared by weighing 10 g poly(ethylene glycol), mean molecular weight 10,000 (Polysciences, Inc.), 0.641 g DESMODUR® N-75 BA/X (Bayer), 148 µL dibutyltin dilaurate, 95% (Sigma-Aldrich Co.), and 100 mL dichloromethane (Sigma-Aldrich Co.) into a 250 mL Erlenmeyer flask. The sample dwelled in the coating formulation for two minutes before being extracted.

After extraction, the coated mandrel was bake cured at 60° C. for 45 minutes. The resulting product was a metallic surface that was rendered to be lubricious when exposed to an aqueous solution.

EXAMPLE 7

Argon Plasma Treated Nitinol Silanized with Triethoxy(Octyl) Silane

A 7" length of nitinol mandrel (0.018" ID) was dip coated in a 5% triethoxy(octyl) silane solution to apply an alkyl surface. Then, the mandrel underwent argon gas plasma treatment to further increase nucleophilic functionality. The argon gas plasma treatment was performed with a gas flow rate of 195 sccm at 126 watts under 500 mtorr of pressure for 5 minutes.

The sample was mechanically dipped into a cross-linked polyol coating formulation prepared by weighing 10 g poly(ethylene glycol), mean molecular weight 10,000 (Polysciences, Inc.), 0.641 g DESMODUR® N-75 BA/X (Bayer), 148 µL dibutyltin dilaurate, 95% (Sigma-Aldrich Co.), and 100 mL dichloromethane (Sigma-Aldrich Co.) into a 250 mL Erlenmeyer flask. The sample dwelled in the coating formulation for two minutes before being extracted.

After extraction, the coated mandrel was bake cured at 60° C. for 45 minutes. The resulting product was a metallic surface that was rendered to be lubricious when exposed to an aqueous solution.

EXAMPLE 8

Nitinol Silanized with 3-(Triethoxysily)propyl isocyanate

A 7" length of nitinol mandrel (0.018" ID) was dip coated in a 5% 3-(triethoxysily)propyl isocyanate solution to apply an alkyl surface and provide nucleophilic functionality.

The sample was mechanically dipped into a cross-linked polyol coating formulation prepared by weighing 10 g poly(ethylene glycol), mean molecular weight 10,000 (Polysciences, Inc.), 0.641 g DESMODUR® N-75 BA/X (Bayer), 148 µL dibutyltin dilaurate, 95% (Sigma-Aldrich Co.), and 100 mL dichloromethane (Sigma-Aldrich Co.) into a 250 mL Erlenmeyer flask. The sample dwelled in the coating formulation for two minutes before being extracted. After extraction, the coated mandrel was bake cured at 60° C. for 45 minutes resulting in a coated nitinol mandrel.

EXAMPLE 9

Determination of Lubricity and Durability of Samples

Lubricity and durability of coated samples from the above Examples were measured using Oak River DL1000 Lubricity and Durability Tester. The samples were placed in a 37° C. circulating de-ionized water bath and pulled through 60D silicone pads. The testing parameters were as follows:

| Test Type | Pull |
| --- | --- |
| Test Distance | 100 mm |
| Number of cycles | 100 |
| Speed | 25 mm/s |
| Acceleration | 200 mm/s |
| Sampling Frequency | 30 Hz |
| Grip Force during Test | 500 g |

Lubricity was determined by calculating the mean grams force of the sample measured over 100 cycles. Durability was determined by measuring the average deviation from the mean of grams force for each of the sample measured over 100 cycles. All samples were tested in triplicate and the results are displayed in Table 1.

TABLE 1

| Substrate | Average Force (g) | Std. Dev. |
| --- | --- | --- |
| Grilamid (Untreated) | 462.1 | 17 |
| Teflon/Polyethylene Coextrusion (Untreated) | 363.2 | 34.6 |
| 304 Stainless Steel (Untreated) | 209.5 | 4.3 |
| Nitinol (Untreated) | 335.4 | 21.8 |
| Argon plasma treated Grilamid (Example 1) | 18.3 | 0.8 |
| Oxygen Plasma Treated Teflon/Polyethylene Coextrusion (Example 3) | 13.3 | 0.7 |
| Argon Plasma Treated 304 Stainless Steel silanized with 3% Trimethoxy(octadecyl) silane (Example 6) | 24.9 | 1.5 |
| Argon Plasma Treated Nitinol silanized with 3% Triethoxy(octyl) silane (Example 7) | 36.1 | 3.7 |

As seen in Table 1, the average force of the untreated samples versus the samples prepared according to the present description was significantly reduced. These results translate into lubricious coated substances/articles that can glide within human tissues and vessels with minimal amounts of force.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method of coating a surface, the method comprising the steps of;
   a) mixing a coating composition comprising at a poly (ethylene) glycol, hexamethylene diisocyanate, dichloromethane, dibutyltin dilaurate, and optionally at least one additional compound having at least two isocyanate groups, wherein the coating composition is biocompatible;
   b) polymerizing the coating composition to form a polymerized coating composition;
   c) creating an active surface on at least two sides of the surface by introducing nucleophilic functional groups onto the surface, wherein the creating step is accomplished using argon or oxygen plasma;
   d) forming a coated surface by maintaining the active surface in the polymerized coating composition for at least about 90 seconds, wherein the polymerized coating composition is deposited directly onto both sides of the active surface without a primer base coat; and
   e) curing the coated surface.

2. The method according to claim 1 wherein the surface is polymeric.

3. The method according to claim 2 wherein the surface contains alkyl carbons.

4. The method according to claim 1 wherein the surface is metallic.

5. The method according to claim 4 further comprising a step after a) wherein the step comprises applying an alkyl carbon containing coating to the metallic surface.

6. The method according to claim 5 wherein the alkyl carbon containing coating is a silane coating.

7. The method according to claim 1 wherein the at least one additional compound having at least two isocyanate groups is selected from 1,4-tetramethylene di-isocyanate, 1,6-hexamethylene di-isocyanate(HDI), trifunctional biuret, isocyanurate derivatives of HDI, p-tetramethylxylene di-isocyanate, trans 1,4-cyclohexylene di-isocyanate, m-xylene di-isocyanate and combinations thereof.

8. A method of coating a surface comprising the steps; maintaining the surface in a coating composition for at least about 90 seconds after the coating composition has polymerized, wherein the coating composition is biocompatible, comprises a polymerized reaction product of poly(ethylene) glycol, hexamethylene diisocyanate, dichloromethane, dibutyltin dilaurate, and optionally at least one additional compound having at least two isocyanate groups, and is deposited directly onto at least two sides of the surface without a primer base coat, and wherein the surface has been treated with argon or oxygen plasma.

9. The method according to claim 8 wherein the surface is polymeric.

10. The method according to claim 8 wherein the surface is metallic.

11. The method according to claim 8 wherein the at least one additional compound having at least two isocyanate groups is selected from 1,4-tetramethylene di-isocyanate, 1,6-hexamethylene di-isocyanate(HDI), trifunctional biuret, isocyanurate derivatives of HDI, p-tetramethylxylene di-isocyanate, trans 1,4-cyclohexylene di-isocyanate, m-xylene di-isocyanate and combinations thereof.

12. The method according to claim 8 wherein the surface is selected from a catheters surface, an introducer sheath surface, a stent surface, an embolic pusher surface, a guide wire surface, an overcoil surface, and combinations thereof.

13. A method of coating an implantable medical device surface comprising the steps of:
   a) providing an implantable medical device;
   b) mixing a coating composition comprising poly(ethylene) glycol, hexamethylene diisocyanate, dichloromethan, dibutyltin dilaurate, and optionally at least one additional compound having at least two isocyanate groups;
   c) polymerizing the coating composition to form a polymerized coating composition;
   d) creating an active surface by argon or oxygen plasma treating the implantable medical device surface;
   e) forming a coated surface by maintaining the active surface in the polymerized coating composition for at least about 90 seconds, wherein the polymerized coating composition is deposited directly onto the active surface without a primer base coat;
   f) curing the coated surface; and
   g) forming a coated implantable medical device.

14. The method according to claim 13 wherein the surface is polymeric.

15. The method according to claim 13 wherein the surface is metallic.

16. The method according to claim 15 further comprising applying an alkyl carbon containing coating to the metallic surface.

17. The method according to claim 13 wherein the at least one additional compound having at least two isocyanate groups is selected from 1,4-tetramethylene di-isocyanate, 1,6-hexamethylene di-isocyanate(HDI), trifunctional biuret, isocyanurate derivatives of HDl, p-tetramethylxylene di-isocyanate, trans 1,4-cyclohexylene di-isocyanate, m-xylene di-isocyanate and combinations thereof.

18. The method according to claim 13 wherein the implantable medical device is selected from catheters, introducer sheaths, stents, embolic pushers, guide wires, overcoils, and combinations thereof.

19. The method according to claim 1, wherein the at least one polyol and the hexamethylene diisocyanate or the additional compound having at least two isocyanate groups are in a ratio of about 1,000 to 1, about 500:1, about 250:1, about 100:1, about 50:1, about 25:1, about 10:1, about 5:1, about 2:1, about 1:1, about 1:2, about 1:5, about 1:10, about 1:25, about 1:50, about 1:100, about 1:250, about 1:500 or about 1:1,000, respectively.

* * * * *